(12) United States Patent
Childs

(10) Patent No.: US 9,399,135 B2
(45) Date of Patent: Jul. 26, 2016

(54) ELECTRONIC STIMULATOR DEVICE PULSE GENERATOR CIRCUIT

(75) Inventor: Jeffrey J. Childs, Eagan, MN (US)

(73) Assignee: Astora Women's Health, LLC, Eden Prairie, MN (US)

( * ) Notice: Subject to any disclaimer, the term of this patent is extended or adjusted under 35 U.S.C. 154(b) by 1049 days.

(21) Appl. No.: 13/547,530

(22) Filed: Jul. 12, 2012

(65) Prior Publication Data

US 2013/0018441 A1 Jan. 17, 2013

Related U.S. Application Data

(60) Provisional application No. 61/506,714, filed on Jul. 12, 2011.

(51) Int. Cl.
*A61N 1/36* (2006.01)

(52) U.S. Cl.
CPC ........ *A61N 1/36125* (2013.01); *A61N 1/36142* (2013.01); *A61N 1/36007* (2013.01); *A61N 1/36107* (2013.01)

(58) Field of Classification Search
CPC ... A61N 1/36; A61N 1/36014; A61N 1/3956; A61N 1/3752
USPC .......................................... 607/5, 37, 66, 74
See application file for complete search history.

(56) References Cited

U.S. PATENT DOCUMENTS

| 4,722,343 | A | * | 2/1988 | Lombardi | .......... A61N 1/36014 600/554 |
|---|---|---|---|---|---|
| 5,036,850 | A | | 8/1991 | Owens | |
| 6,354,991 | B1 | | 3/2002 | Gross et al. | |
| 6,652,449 | B1 | | 11/2003 | Gross et al. | |
| 6,712,772 | B2 | | 3/2004 | Cohen et al. | |
| 6,862,480 | B2 | | 3/2005 | Cohen et al. | |
| 7,613,516 | B2 | | 11/2009 | Cohen et al. | |
| 2010/0114258 | A1 | * | 5/2010 | Donofrio | ................. A61N 1/37 607/63 |

* cited by examiner

*Primary Examiner* — Catherine Voorhees
*Assistant Examiner* — Roland Dinga
(74) *Attorney, Agent, or Firm* — Brian D. Kaul; Westman, Champlin & Koehler, P.A.

(57) ABSTRACT

An electronic stimulator device comprises a battery, first and second output ports, and an energy discharge circuit. The energy discharge circuit is coupled to the battery and configured to receive an electrical charge from the battery and deliver the electrical charge through an energy output port. A first switch is connected between the energy output and the first output port. A second switch is connected between the second output port and electrical ground. A third switch is connected between the second output port and the energy output. A fourth switch is connected between the first output port and electrical ground. A controller comprising a processor is configured to actuate the first, second, third and fourth switches between open and close states to deliver a biphasic current pulse between the first and second output ports.

10 Claims, 6 Drawing Sheets

ELECTRONIC STIMULATOR DEVICE PULSE GENERATOR CIRCUIT

CROSS-REFERENCE TO RELATED APPLICATION

This application claims the benefit of U.S. Provisional Application Ser. No. 61/506,714 filed Jul. 12, 2011, the content of which is hereby incorporated by reference in its entirety.

FIELD OF THE INVENTION

Embodiments of the invention are directed to pulse generator circuits for use in electronic stimulator devices that provide biphasic therapy current pulses with reduced or eliminated switching transients caused by the energy stored in parasitic capacitances of semiconductor switches such as Field Effect Transistors (FET's). Other embodiments are directed to the discharge of residual energy in the pulse generator circuit.

BACKGROUND

Implantable electronic stimulator devices, such as neuromuscular stimulation devices, have been disclosed for use in the treatment of various pelvic conditions, such as urinary incontinence, fecal incontinence and sexual dysfunction. Such devices generally include one or more electrodes that are coupled to a control unit by electrode leads. Current pulses, such as biphasic pulses, are applied to the desired pelvic tissue of the patient through the electrode leads in order to treat the condition of the patient. Exemplary implantable electronic stimulator devices and uses of the devices are disclosed in U.S. Pat. Nos. 6,354,991, 6,652,449, 6,712,772 and 6,862,480, each of which is hereby incorporated by reference in its entirety.

Parasitic capacitances may develop in semiconductor switches of pulse generator circuits. Such parasitic capacitances may prevent the pulse generator from accurately producing current pulses of a prescribed stimulation therapy.

SUMMARY

Embodiments of the invention are directed to an electronic stimulator device comprising a pulse generator circuit configured to deliver a biphasic electrical stimulation therapy to tissue of a patient, and a method of using the device to deliver a biphasic electrical stimulation therapy to tissue of a patient. One embodiment of the device comprises a battery, first and second output ports, and an energy discharge circuit. The energy discharge circuit is coupled to the battery and configured to receive an electrical charge from the battery and deliver the electrical charge through an energy output port. A first switch is connected between the energy output and the first output port. A second switch is connected between the second output port and electrical ground. A third switch is connected between the second output port and the energy output. A fourth switch is connected between the first output port and electrical ground. A controller comprising a processor is configured to actuate the first, second, third and fourth switches between open and close states to deliver a biphasic current pulse between the first and second output ports.

In one embodiment of the method, the device described above is provided. First and second electrodes are coupled to the first and second output ports and are implanted in tissue of a patient. A first current pulse is delivered to the tissue of the patient by placing the first and second switches in the closed state and the third and fourth switches in the open state using the controller. The first current pulse is delivered from the energy output through the first switch, the first output port, the first electrode, the tissue, the second electrode, the second output port and to electrical ground through the second switch.

Other features and benefits that characterize embodiments of the present invention will be apparent upon reading the following detailed description and review of the associated drawings.

DETAILED DESCRIPTION OF ILLUSTRATIVE EMBODIMENTS

Figure 1:
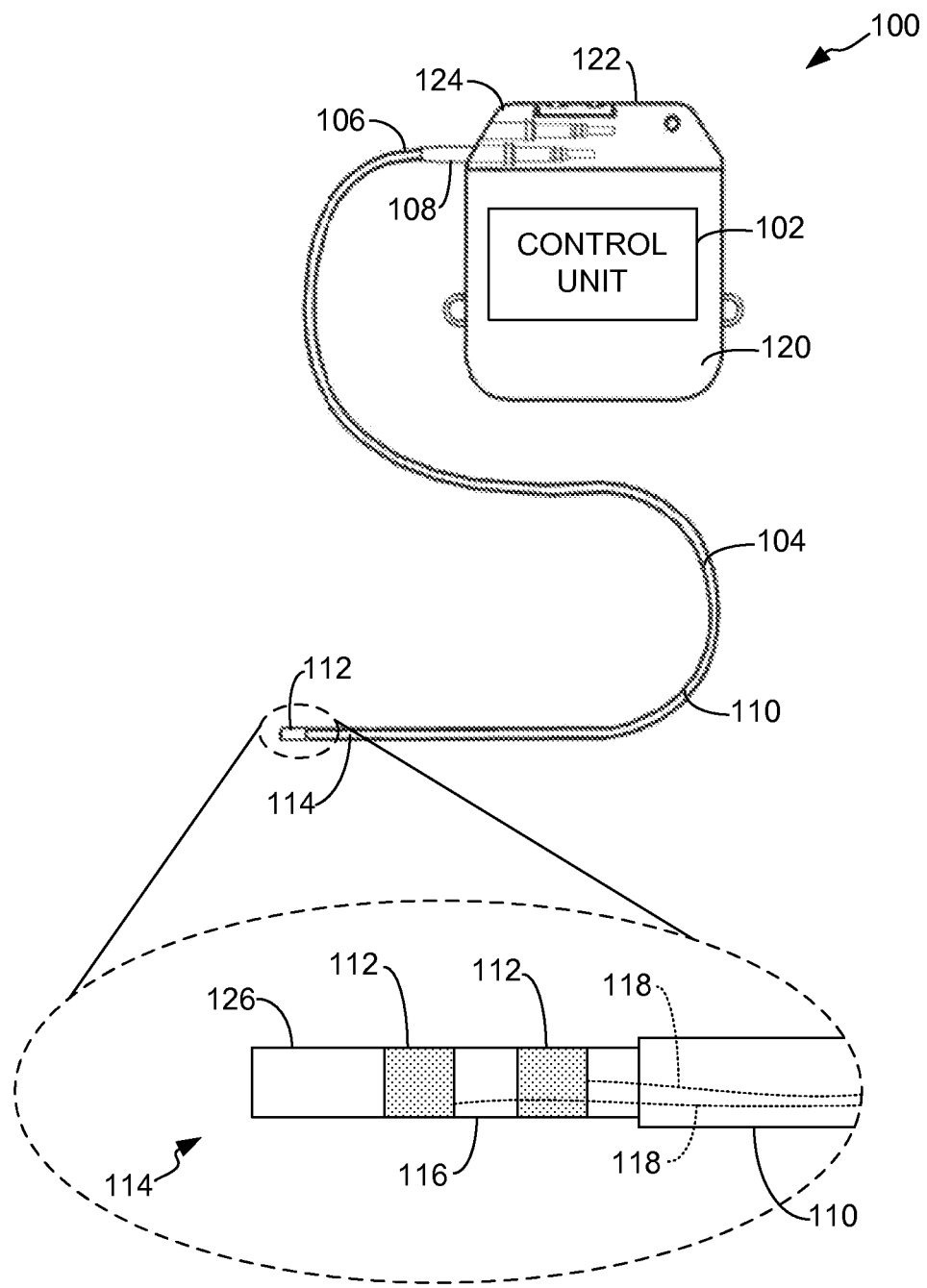
FIG. 1 is a side plan view of an exemplary electronic stimulator device in accordance with embodiments of the invention.

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art, and will not be interpreted in an idealized or overly formal sense unless expressly so defined herein.

FIG. 1 is a side plan view of an exemplary electronic stimulator device 100 formed in accordance with one or more embodiments of the invention describe herein. In one embodiment, the stimulator device 100 is configured for implantation into a pelvic region of a patient to provide muscle and/or nerve stimulation that is used to control and/or treat a pelvic condition of the patient, such as pelvic pain, urinary incontinence, fecal incontinence, erectile dysfunction or other pelvic condition that may be treated through electrical stimulation.

In one embodiment, the device 100 comprises a control unit 102 and one or more electrode leads 104, a proximal end 106 of which is electrically coupled to the control unit 102 via a connector 108. Each electrode lead 104 comprises a lead body 110 and one or more stimulation elements or electrodes 112 attached to a distal end 114 of the lead body 110. In one embodiment, the electrodes 112 are separated from each other by an insulative portion or element 116. The lead body 110 insulates electrical wires 118 connecting the control unit 102 to the electrodes 112. The lead body 110 can be in the form of an insulating jacket typically comprising silicone, polyurethane, or other flexible, biocompatible, and electrically insulating material. Additional electrode leads 104 or physiological sensors may be coupled to the control unit 102.

In one embodiment, the control unit 102 comprises circuitry including at least one processor for processing electrical signals received from the one or more electrodes 112 or physiological sensors (not shown). In one embodiment, the control unit 102 includes a pulse generator circuit in accordance with one or more embodiments described herein, which is configured to generate current pulses that are delivered to tissue of a patient through the one or more electrodes 112.

In one embodiment, the control unit 102 is enclosed within a hermetically sealed metal housing 120 commonly referred to as a "can." The can 120 generally comprises first and second halves that are joined together in a laser-welding operation about their perimeters after the battery power supply and electronic circuitry are inserted in the space defined by the two halves of the can.

A header 122 includes a connector block 124 that may be molded in the header or inserted after the header has been molded. Feed-through conductors from the electronic circuitry within the can 120 are coupled to electrical contacts of the connector block 124. The connector block 124 includes one or more ports, each of which receives the connector 108 of each lead 104 and electrically couples the connector 108 to the electronic circuitry of the control unit 102 via the feed-through conductors.

The distal end 114 of the electrode lead 104 can be anchored to pelvic tissue of the patient (e.g., urinary sphincter muscle, anal sphincter muscle, etc.) by means of a tissue anchor 126, such as a helical coil or other tissue anchor. The anchor 126 operates to secure the position of the electrodes 112 in the desired tissue of the patient.

Figure 2:
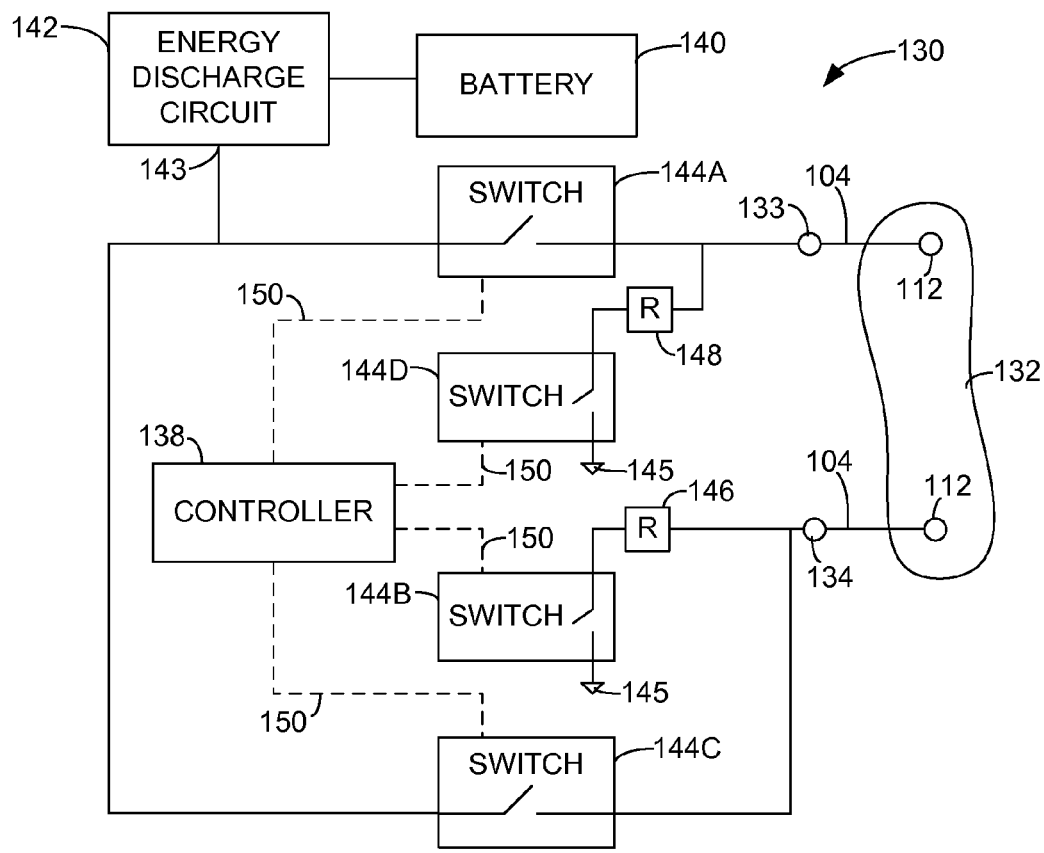
FIG. 2 is a schematic diagram of a pulse generator circuit 130 for use in an electronic stimulator device in accordance with embodiments of the invention.

FIG. 2 is a schematic diagram of a pulse generator circuit 130 for use in an electronic stimulator device, such as in the control unit 102 in the electronic stimulator device 100 described above. In one embodiment, the circuit 130 is configured to deliver a biphasic pulse through output ports 133 and 134, which may be electrically coupled to the tissue 132 through one or more electrodes 112, to provide a desired electrical stimulation therapy.

Figure 3:
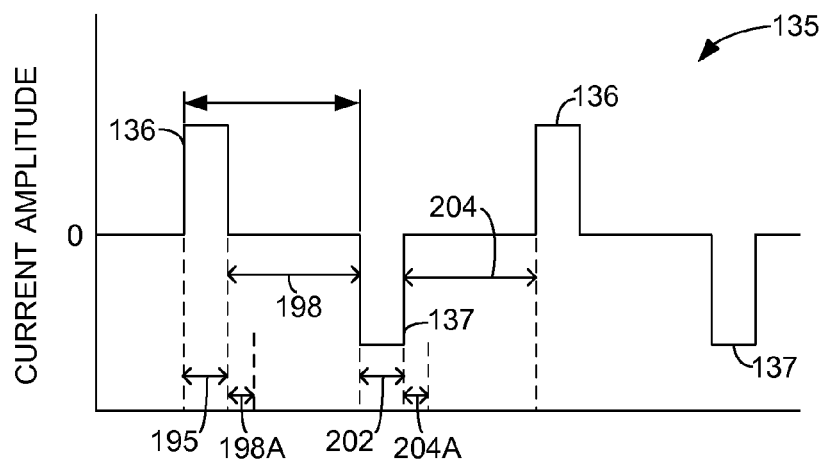
FIG. 3 is a graph of an exemplary biphasic waveform in accordance with embodiments of the invention.

FIG. 3 is a graph of an exemplary biphasic waveform 135 delivered to tissue 132 of a patient through the output port 133. The waveform 135 comprises positive current or current pulses 136 and negative current or current pulses 137. As used herein, a "positive current pulse" is a current pulse that travels from the output port 133 to the tissue 132. In some embodiments, the positive current pulse returns to the circuit 130 through the output port 134 where it is dissipated to electrical ground or common. As used herein, a "negative current pulse" is a current pulse that is delivered to the tissue 132 through the output port 134 and returns through output port 133 to the circuit 130 where it is dissipated to electrical ground.

In some embodiments, the pulse generator circuit 130 includes a controller 138 comprising one or more processors and memory (e.g., random access memory (RAM), read-only memory (ROM), erasable programmable read-only memory (EPROM or Flash memory, etc.), which are not shown in order to simplify the illustration. The processors are configured to execute program instructions stored in the memory to carry out method steps describe herein. In some embodiments, the controller 138 comprises a micro-controller unit.

In one embodiment, the circuit 130 includes a battery 140 and an energy discharge circuit 142. The battery 140 is used to charge one or more capacitors within the energy discharge circuit 142, in accordance with conventional techniques. The electrical charge on the capacitors is discharged as a current through an energy output 143, which is delivered to the tissue 132 of the patient through the output ports 133 and 134.

In one embodiment, the circuit 130 includes semiconductor switches 144A-144D. In one embodiment, the switch 144A is connected between the energy output 143 and the output port 133, as shown in FIG. 2. In one embodiment, the switch 144B is connected between the output port 134 and electrical ground 145 (represented by an arrow). In one embodiment, a current-limiting resistor 146 is placed in line between the switch 144B and the output port 134, as shown in FIG. 2. In one embodiment, the switch 144C is connected between the output port 134 and the energy output 143. In one embodiment, the switch 144D is connected between the output port 133 and electrical ground. In one embodiment, a current-limiting resistor 148 is connected in series with the switch 144D and the output port 133.

In one embodiment, the controller 138 controls the switches 144A-D, generally referred to as 144, to provide the desired positive current pulse 136 or negative current pulse 137, shown in FIG. 3. The controller 138 controls the opening and closing of the switches 144 through suitable control lines 150, which are illustrated as dashed lines in FIG. 2. The control lines 150 enable the controller to deliver a high voltage control signal (e.g., 5 volts) or a low voltage control signal (e.g., 0 volts) to the switches 144. The control signals from the controller 138 operate to place each of the switches 144 in a closed or enabled state, in which current is allowed to flow through the switch, or an open or disabled state, in which current is prevented from flowing through the switch.

In one embodiment, the controller 138 controls the semiconductor switches 144 in a sequence that eliminates transient spikes and glitches. In one embodiment, the controller 138 enables one pair of the switches 144 at a time in order to develop a differential voltage across the tissue load 132 presented electrically to the output ports 133 and 134, and deliver either a positive current pulse 136, or a negative current pulse 137 through the output ports 133 and 134, to the tissue 132.

Figure 4:
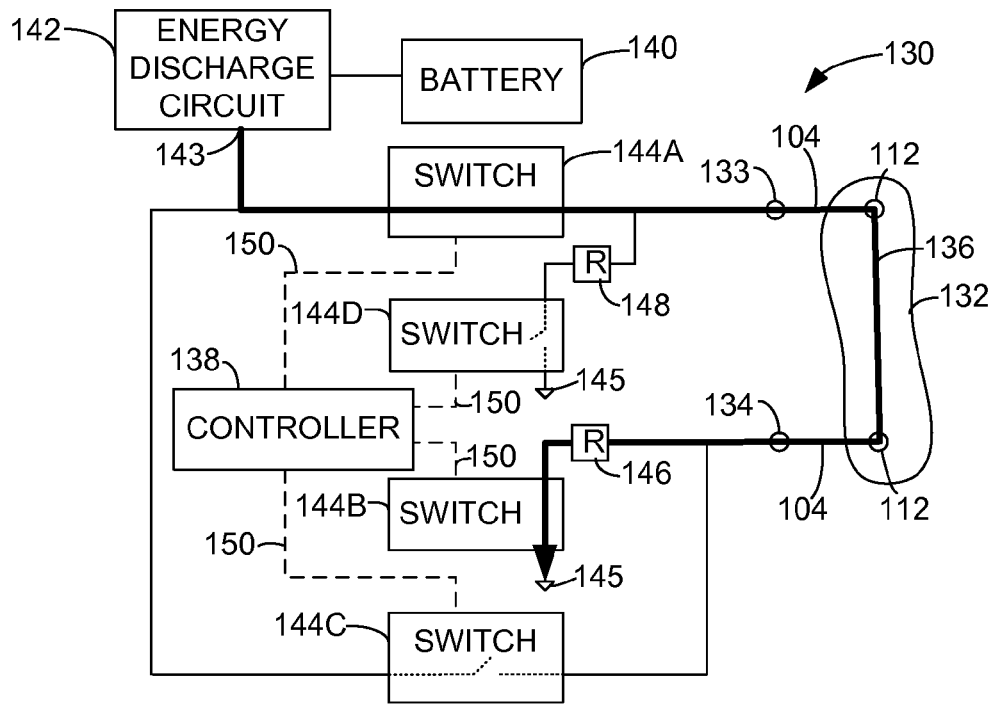
FIGS. 4 and 5 are schematic diagrams of a pulse generator circuit respectively delivering positive and negative current pulses to tissue of a patient in accordance with embodiments of the invention.

In one embodiment, the delivery of a positive pulse 136 (FIG. 3) is achieved by closing switch 144A and switch 144B while switches 144C and 144D are placed in the open or disabled state in response to the appropriate control signal from the controller 138. As shown in the simplified circuit diagram of FIG. 4, this configuration of the switches 144 allows for a positive current pulse 136 (dark arrow) to be delivered from the energy output 143 through the switch 144A, the output port 133, and to the tissue 132. The positive current pulse 136 returns to the pulse generator circuit 130 through the output port 134 where it is delivered to electrical ground 145 through the switch 144B. The current-limiting resistor 146 prevents the magnitude of the positive electrical current pulse from exceeding a desired limit that may damage the tissue 132 or components of the pulse generator circuit 130.

Figure 5:
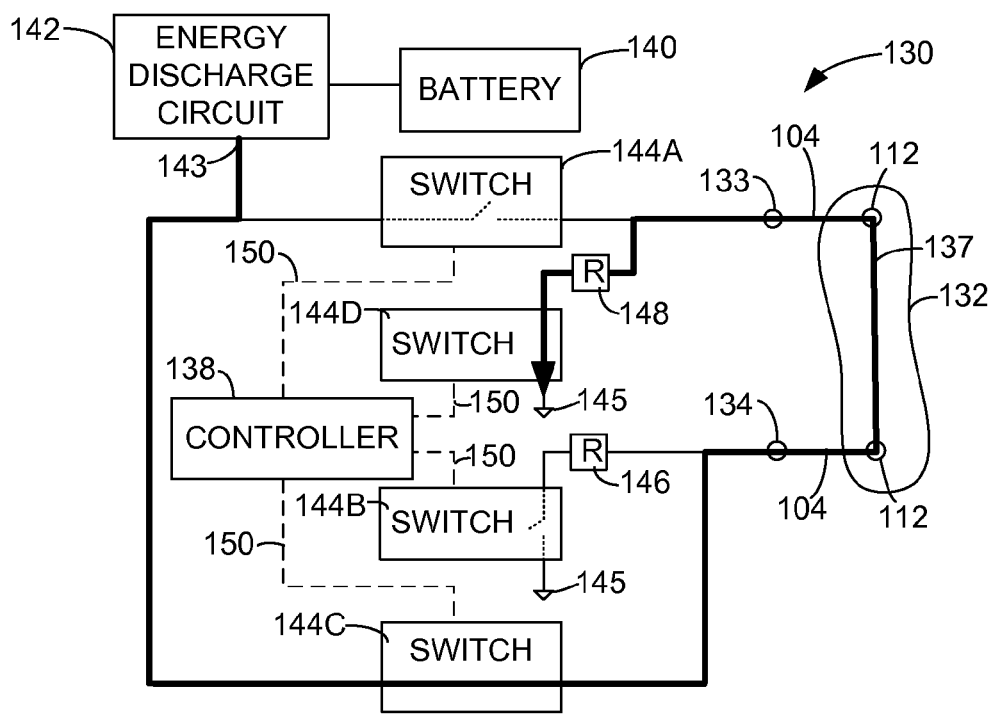

In one embodiment, the controller 138 delivers a negative current pulse 137 (FIG. 3) to the tissue 132 through the output port 134 by placing the switches 144A and 144B in the open or disabled state, and the switches 144C and 144D in the closed or enabled state, as shown in FIG. 5. Here, a differential voltage is generated between the energy output 143 and the electrical ground 145 coupled to the switch 144D. As a result, the negative current pulse 137 is delivered from the energy output 143 through the switch 144C and the output port 134 to the tissue 132. The negative current pulse 137 returns to the pulse generator circuit 130 through the output port 133 where it is delivered to electrical ground 145 through the resistor 148 and the switch 144D. The current-limiting resistor 148 limits the magnitude of the negative current pulse 137 to prevent damage to the tissue 132 and components of the pulse generator circuit 130.

Figure 6:
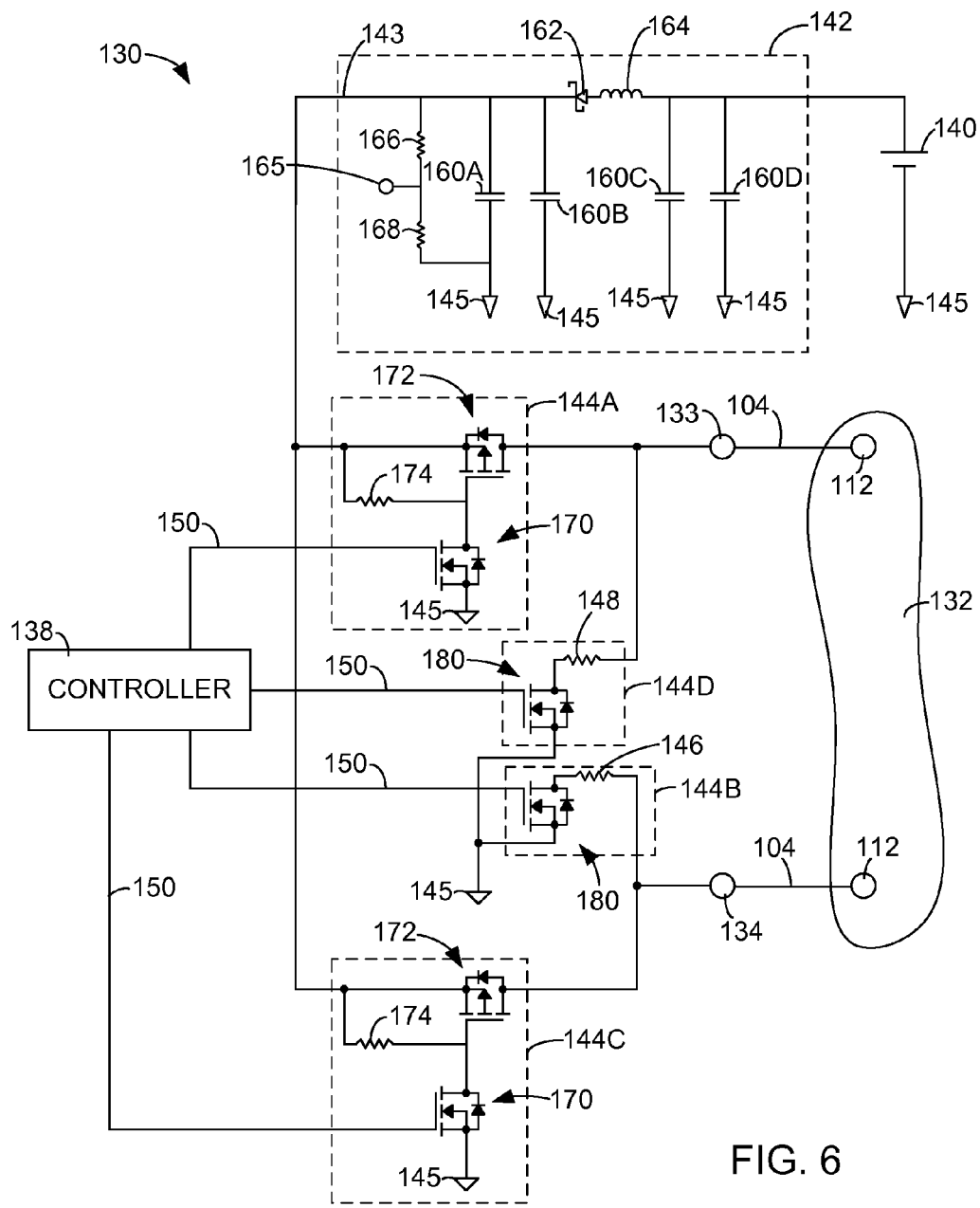
FIG. 6 is a circuit diagram of an exemplary pulse generator circuit in accordance with embodiments of the invention.

FIG. 6 is a circuit diagram of the pulse generator circuit 130 in accordance with exemplary embodiments. In one embodiment, the energy discharge circuit 142 comprises four capacitors 160A-D connected in parallel. A Schottky diode 162 and an inductor 164 are coupled in series between the pair of capacitors 160A and 160B and the pair of capacitors 160C and 160D. The battery 140 delivers electrical charge to the capacitors 160A-160D. The controller 138 may receive a voltage measurement at 165 between resistors 166 and 168 of a voltage divider. The voltage measurement at 165 may be used by the controller 138 to indicate whether the energy discharge circuit 142 is prepared to deliver a desired current pulse.

Embodiments of the switches 144 comprise Field Effect Transistors (FET). In one embodiment, the switches 144A and 144C each comprise a p-channel FET 172 and an n-channel FET 170. The gate of the FET 170 is coupled to the controller 138 through one of the control lines 150. The drain of the FET 170 is coupled to the gate of the FET 172, and the source of the FET 170 is coupled to electrical ground 145. The drains of the FET's 172 are coupled to the energy output 143. The gates of the FET's 172 are coupled to the energy output 143 through a resistor 174. The drain of the FET 172 of the switch 144A is coupled to the output port 133, and the drain of the FET 172 of the switch 144C is coupled to the output port 134. When the controller 138 supplies a low voltage control signal to the gates of the FET's 170, the FET 170 is open and the voltage at the gates of the FET's 172 becomes substantially equal to the voltage at the sources of the FET's 172 to place the FET's 172 and the switches 144A and 144C in the open state. When the controller 138 supplies a high voltage control signal to the gates of the FET's 170, the FET's 170 are placed in the closed state and current is allowed to flow from the energy output 143 through the resistors 174 and to electrical ground 145 through the FET's 170. This places the gates of the FET's 172 at a low voltage relative to the voltage at the sources of the FET's 172, and causes the FET's 172 and the corresponding switches 144A and 144C to be placed in the closed state, in which current may pass from the source to the drain and to the corresponding output port 133 or 134.

The exemplary embodiments of the switches 144B and 144D provided in FIG. 6 each comprise a n-channel FET 180. The gate of the FET 180 is coupled to the controller 138 through the corresponding control line 150, and the source is coupled to electrical ground 145. The FET 180 of the switch 144B is electrically coupled to the output port 134 through the resistor 146, and the FET 180 of the switch 144D is electrically coupled to the output port 133 through the resistor 148. When the controller 138 supplies a low voltage control signal to the gates of the FET's 180, the FET's 180 are placed in the open state and current is prevented from traveling from the drain to the source and, therefore, current is blocked from traveling through the switches 144B and 144D to electrical ground 145. When the controller 138 provides a high voltage control signal to the gates of the FET's 180, the FET's 180 are placed in the closed state allowing current to travel from the drain to the source and on to electrical ground 145.

Figure 7:
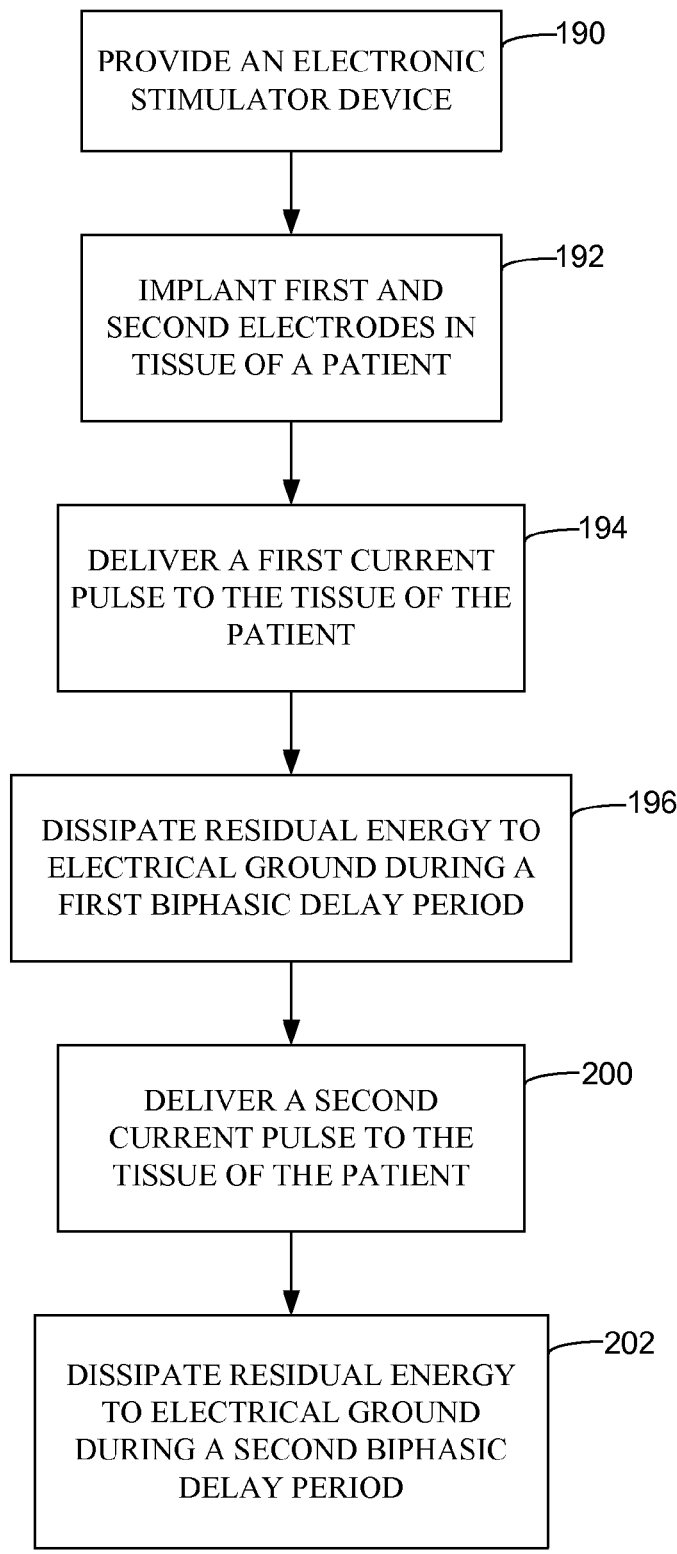
FIG. 7 is a flowchart illustrating a method in accordance with embodiments of the invention.

FIG. 7 is a flowchart illustrating a method in accordance with embodiments of the invention. In one embodiment of the method, an electronic stimulator device 100 (FIG. 1) formed in accordance with one or more embodiments described herein is provided at 190. In one embodiment, the electronic stimulator device 100 comprises first and second electrodes 112 and a pulse generator circuit 130 formed in accordance with one or more embodiments described herein, such as shown in FIGS. 2 and 6. In one embodiment, the electrodes 112 are implanted in tissue 132 of the patient, as indicated at 192.

In one embodiment of the method, a first current pulse is delivered to the tissue 132 of the patient, at 194. In one embodiment, the first current pulse is a positive pulse 136 (FIG. 3), which is delivered in accordance with the embodiments described with reference to FIG. 4. In one embodiment, the delivery of the first current pulse to the tissue 132 of the patient in step 194 comprises the termination of the first current pulse after a predetermined pulse width period 195, as shown in FIG. 3. In one embodiment, the current pulse is terminated by placing the switch 144B in the open state responsive to an appropriate control signal from the controller 138, which eliminates the voltage differential between the output ports 133 and 134. In accordance with exemplary embodiments, the pulse width period 195 is in the range of 40-100 microseconds.

Figure 8:
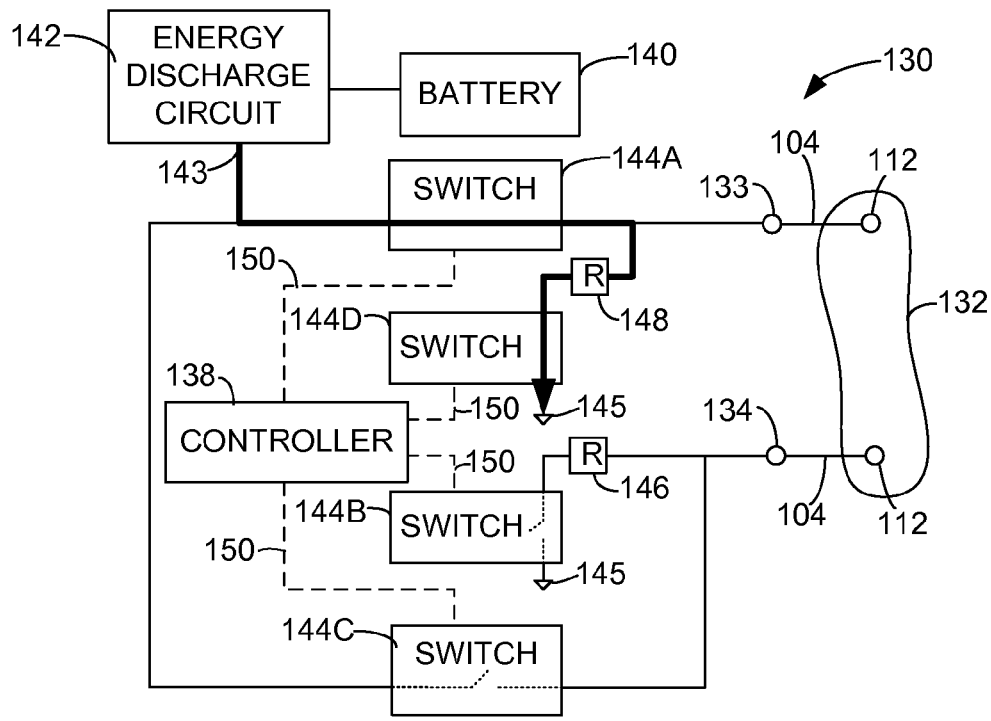
FIGS. 8 and 9 are schematic diagrams of a pulse generator circuit in energy dissipation modes in accordance with embodiments of the invention.

In accordance with one embodiment of the method, at 196, residual energy is dissipated to electrical ground 145 during a first biphasic delay period 198, which is illustrated in FIG. 3. This residual electrical energy may be stored in the parasitic capacitances of the semiconductor switches 144 of the pulse generator circuit 130. The dissipation of this electrical energy prevents the undesirable discharge of transient currents to the tissue 132 of the patient. In one embodiment of step 196, the residual electrical energy stored in the switch 144A and, possibly, the energy discharge circuit 142, is dissipated to electrical ground 145 through the resistor 148 and the switch 144D, as illustrated in the simplified diagram of the pulse generator circuit 130 provide in FIG. 8. Switches 144A and/or 144D may be cycled between the closed and open states by controller 138 to avoid overheating the resistor 148. In one embodiment, the duty cycle of the closed or enabled states is approximately 2%.

In one embodiment, the switch 144A is transitioned from the closed state to the open state responsive to the control signal from the controller 138 over a first portion 198A (FIG. 3) of the first biphasic delay period 198 of step 196. Residual energy stored in the switch 144A, the energy discharge circuit 142, and the output port 133 is dissipated to electrical ground 145 during this delayed transition of the switch 144A from the closed state to the open state. In one embodiment, the switch 144D is placed in the closed state responsive to a control signal from the controller 138 during the first biphasic delay period 198 to deliver the residual energy stored in the switch 144A to electrical ground 145. In one embodiment, the switch 144D is held in the closed state until the end of the first biphasic delay period responsive to a control signal from the controller 138. This ensures that all of the residual energy stored in the switch 144A is dissipated to electrical ground 145.

In one exemplary embodiment, the delayed transition of the switch 144A from the closed state to the open state over the first portion of 198A of the first biphasic delay period 198 of approximately 200 microseconds is made possible by the configuration of the exemplary switch 144A provided in FIG. 6. During the transition of the switch 144A to the open position, the controller 138 changes the high voltage control signal on the gate of the FET 170 to a low voltage control signal. This places the FET 170 in the open state. Initially, current is allowed to flow through the resistor 174 (e.g., 300k ohm) due to the voltage differential between the energy output 143 and the drain of the FET 170. At the end of the first portion 198A of the first biphasic delay period 198, the voltage difference between the gate and source of the FET 172 reaches a threshold difference that transitions the FET 172 to the open state. In one embodiment, the end of the first portion 198A is followed by an additional delay of approximately 13.5 milliseconds to complete the first biphasic delay period. Other delay periods may also be used.

At 200 of the method, a second current pulse is delivered to the tissue 132 of the patient. In one embodiment, the second current pulse is in the form of a negative pulse 137, shown in FIG. 3. In one embodiment, the second current pulse is delivered to the tissue 132 of the patient immediately following the first biphasic delay period 198. The second current pulse may be delivered to the tissue 132 by opening switches 144A and 144B, and closing switches 144C and 144D responsive to control signals from the controller 138 as discussed above with reference to FIG. 5. In one embodiment, the delivery of the second current pulse 137 is terminated after a predetermined pulse width period 202 (FIG. 3) by opening switch 144D. This eliminates the voltage differential between the output ports 133 and 134, and prevents the further delivery of current to the tissue 132.

Figure 9:
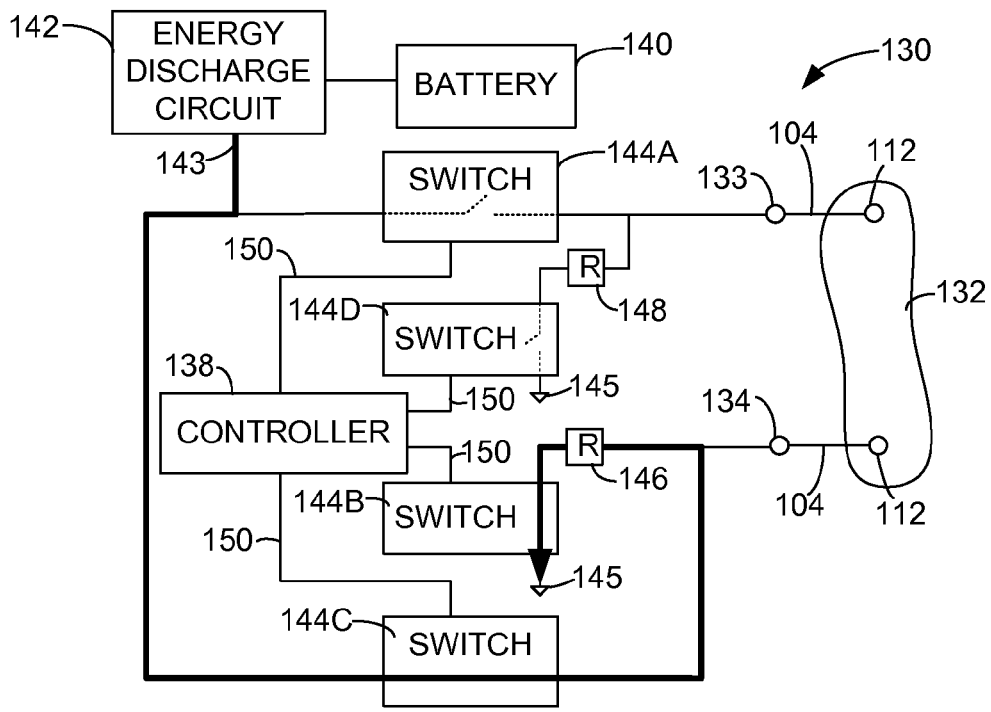

In one embodiment of the method, residual energy is dissipated to electrical ground 145 during a second biphasic delay period 204 (FIG. 3), as indicated at step 202. In one embodiment of step 202, switch 144B is placed in the closed state in response to a control signal from the controller 138. This allows residual energy in the switch 144C, the energy discharge circuit 142, and the output port 134 to be delivered to electrical ground 145 through the resistor 146 and the switch 144B, as shown in FIG. 9. Switches 144B and/or 144C may be cycled between the closed and open states by controller 138 to avoid overheating the resistor 146. In one embodiment, the duty cycle of the closed or enabled states is approximately 2%.

In one embodiment, the switch 144C is transitioned from the closed state to the open state responsive to a control signal from the controller 138 over a first portion 204A (FIG. 3) of the second biphasic delay period 204 of approximately 200 microseconds. In one embodiment, the switch 144C has the exemplary configuration provided in FIG. 6, which operates in the same manner as exemplary switch 144A discussed above to provide the slow transition of the switch 144C from the closed state to the open state responsive to control signals from the controller 138. In one embodiment, the end of the first portion 204A is followed by an additional delay of approximately 13.5 milliseconds to complete the second biphasic delay period. Other delay periods may also be used.

Embodiments of the method include repeating steps 194, 196, 200 and 202 as necessary to provide the desired biphasic electrical stimulation therapy to the tissue 132 of the patient. The amplitude and the pulse width periods of the current pulses 136 and 137, and the biphasic delay periods 198 and 204 may be set to provide the desired physiological response. As a result, embodiments of the method allow for electrical stimulation therapies to be delivered to tissue 132 of a patient in a balanced, biphasic manner so that no unintended differential current spikes flow to the tissue 132 through the output ports 133 and 134.

Energy may also be dissipated from the energy discharge circuit 142 without delivering energy to the patient through the output terminals 133 and 134. This is generally accomplished by maintaining the switch 144A in the closed position as energy is dissipated through the switch 144D (FIG. 8), or by maintaining the switch 144C in the closed position as energy is dissipated through electrical ground 145 through the switch 144B, as shown in FIG. 9. This may be useful when the voltage at the energy output 143 needs to be adjusted downward before further pulses are delivered to the patient, for example. This discharge of the voltage of the energy discharge circuit 142 is accomplished without exceeding the power rating of the components of the circuit 130 due to, for example, the dissipation of the energy through current-limiting resistors 148 and 146. Additionally, the controller 138 can modulate the open and closed states of the switches 144B and 144D to impose a duty cycle on the dissipation of the electrical energy to electrical ground 145 as necessary.

Although the present invention has been described with reference to preferred embodiments, workers skilled in the art will recognize that changes may be made in form and detail without departing from the spirit and scope of the invention.

What is claimed is:

1. An electronic stimulator device comprising:
   a battery;
   first and second output ports each configured to electrically couple to an electrode lead;
   an energy discharge circuit coupled to the battery, the energy discharge circuit configured to receive an electrical charge from the battery and deliver the electrical charge through an energy output;
   a first switch connected between the energy output and the first output port;
   a second switch connected between the second output port and electrical ground;
   a third switch connected between the second output port and the energy output;
   a fourth switch connected between the first output port and electrical ground; and
   a controller comprising a processor configured to actuate the first, second, third and fourth switches between open and closed states to deliver a biphasic current pulse between the first and second output ports.

2. The device of claim 1, wherein:
   the controller places the first and second switches in the closed state, and the third and fourth switches in the open state, wherein a first current pulse having a first polarity between the first and second output ports; and
   the controller places the first and second switches in the open state, and the third and fourth switches in the closed state to deliver a second current pulse having a second polarity that is opposite the first polarity between the first and second output ports.

3. The device of claim 2, wherein:
the controller places the second switch in the open state after a predetermined pulse width period to terminate the delivery of the first current pulse between the first and second output ports; and
the controller places the fourth switch in the open state after a predetermined pulse width period to terminate the delivery of the second current pulse between the first and second output ports.

4. The device of claim 3, wherein the controller implements a first biphasic delay period after the delivery of the first current pulse between the first and second output ports, during which no current pulses are delivered between the first and second output ports and residual energy is dissipated through the fourth switch to electrical ground.

5. The device of claim 4, wherein the first switch transitions from the closed state to the open state responsive to a control signal from the controller over a first portion of the first biphasic delay period, and the controller places the fourth switch in the closed state until the end of the first biphasic delay period.

6. The device of claim 5, wherein the first switch comprises:
an n-channel field effect transistor (FET) having a source electrically coupled to the energy output, a drain electrically coupled to the first output port, and a gate electrically coupled to the energy output through a resistor; and
a p-channel FET having a source electrically coupled to the gate of the n-channel FET, a drain electrically coupled to electrical ground, and a gate electrically coupled to the controller.

7. The device of claim 5, wherein the controller implements a second biphasic delay period after the delivery of the second current pulse between the first and second output ports, during which no current pulses are delivered between the first and second output ports and residual energy is dissipated through the second switch to electrical ground.

8. The device of claim 7, wherein the third switch transitions from the closed state to the open state responsive to a control signal from the controller over a first portion of the second biphasic delay period, and the controller places the second switch in the closed state until the end of the second biphasic delay period.

9. The device of claim 8, wherein the third switch comprises:
an n-channel field effect transistor (FET) having a source electrically coupled to the energy output, a drain electrically coupled to the second output port, and a gate electrically coupled to the energy output through a resistor; and
a p-channel FET having a source electrically coupled to the gate of the n-channel FET, a drain electrically coupled to electrical ground, and a gate electrically coupled to the controller.

10. The device of claim 8, further comprising a hermetically sealed housing containing the battery, the energy discharge circuit, the first switch, the second switch, the third switch, the fourth switch, and the controller.

* * * * *